United States Patent [19]

Christopher

[11] Patent Number: 4,710,169
[45] Date of Patent: Dec. 1, 1987

[54] URINARY CATHETER WITH COLLAPSIBLE URETHRAL TUBE

[76] Inventor: T. Graham Christopher, 8727 Talbot Rd., Edmonds, Wash. 98020

[21] Appl. No.: 805,546

[22] Filed: Dec. 11, 1985

Related U.S. Application Data

[63] Continuation-in-part of Ser. No. 562,094, Dec. 16, 1983, Pat. No. 4,571,241.

[51] Int. Cl.$^4$ ............................................. A61M 25/00
[52] U.S. Cl. ................................... 604/104; 604/171; 604/265; 128/DIG. 25
[58] Field of Search ...................... 604/104, 105, 93.96, 604/280, 282, 256, 247, 265, 172, 171; 128/DIG. 25

[56] References Cited

U.S. PATENT DOCUMENTS

| | | | |
|---|---|---|---|
| 1,120,549 | 12/1914 | Schellberg | 604/171 |
| 3,344,791 | 10/1967 | Foderick . | |
| 3,394,705 | 7/1968 | Abramson . | |
| 3,428,046 | 2/1969 | Remer et al. . | |
| 3,556,294 | 1/1971 | Walck, III | 604/172 X |
| 3,769,981 | 11/1973 | McWhorter . | |
| 3,898,993 | 8/1975 | Taniguchi | 604/172 |
| 4,062,363 | 12/1977 | Bonner, Jr. | 604/171 |
| 4,100,923 | 7/1978 | Southern | 604/96 X |
| 4,349,029 | 9/1982 | Mott . | |
| 4,553,959 | 11/1985 | Hickey et al. | 604/105 X |

Primary Examiner—Stephen C. Pellegrino
Attorney, Agent, or Firm—Christensen, O'Connor, Johnson & Kindness

[57] ABSTRACT

An indwelling urinary catheter having semi-rigid tubular portions for holding open the entrance of the bladder and the urethral exit and a collapsible tubular portion extending through the urethra. The collapsible tube is closed by the normal urethral mechanism and opened upon the flow of urine, thus blocking bacterial migration into the body and avoiding abnormal, continuous distention of the urethra and consequent discomfort to the patient. Avoided, as well, is the transmission of infection occasioned by the sliding motion of rigid-tube catheters within the urethra.

2 Claims, 12 Drawing Figures

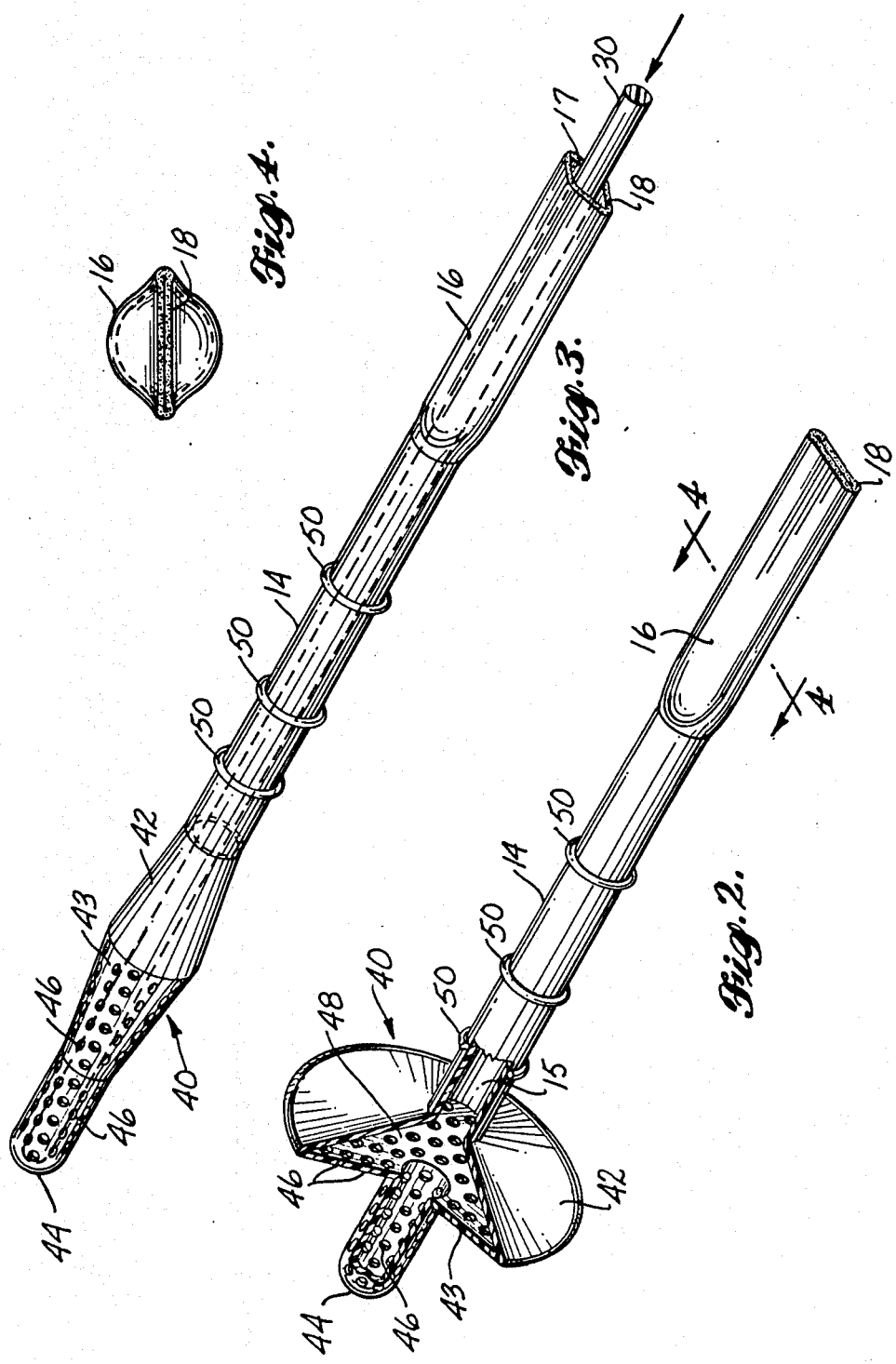

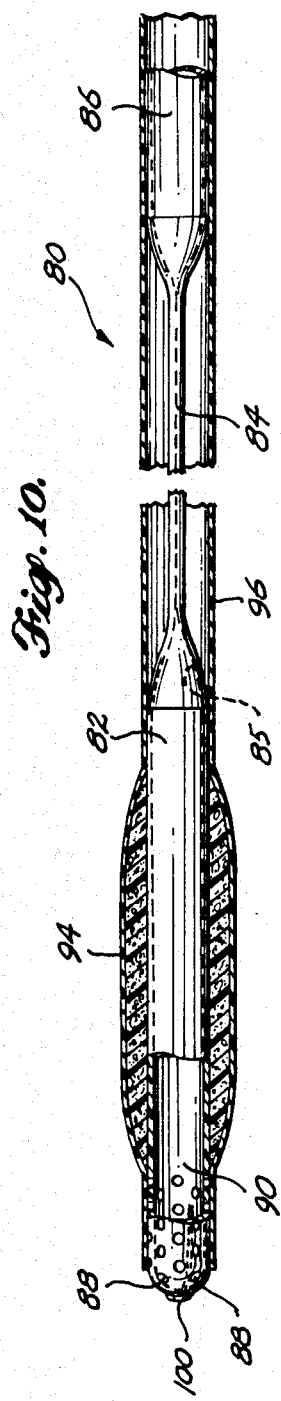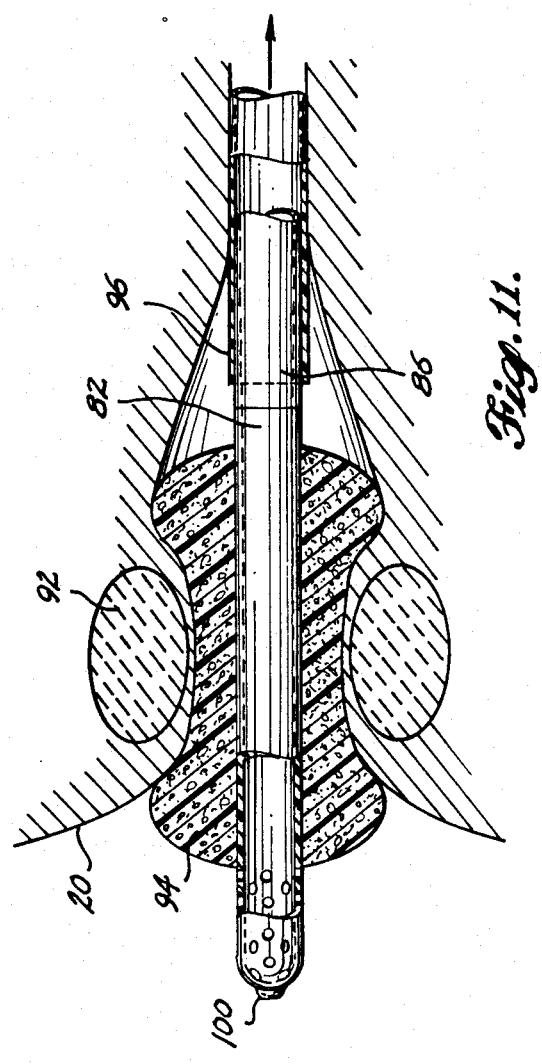

URINARY CATHETER WITH COLLAPSIBLE URETHRAL TUBE

CROSS-REFERENCE TO RELATED APPLICATIONS

This is a continuation-in-part of U.S. application Ser. No. 562,094, filed Dec. 16, 1983 now U.S. Pat. No. 4,571,241.

BACKGROUND OF THE INVENTION

The present invention relates generally to urinary catheters and, more particularly, to indwelling catheters, which permit the continuous collection of urine while reducing irritation of the urethra and diminishing the likelihood of bacterial migration into the bladder.

in general, urinary catheters are intended to permit continuing collection or urine without leakage into a patient's clothing and bedding. To accomplish these functions, such catheters typically include means for retaining the catheter within the bladder, means for defeating the sphincter valve mechanism that normally closes the urethra, and a sterile system for transferring the collected urine to a suitable container.

The standard Foley catheter is a typical example of this type of retained urinary catheter. In simplest form, such catheters consist of a thickwalled elastic tube with an inflatable balloon at the end, which is inserted into the bladder. Although flexible enough to follow the curvature of the urethra to permit insertion, the tube is radially rigid in order to continually distend the urethra and neck of the bladder to allow continuous drainage of urine into a connected sterile tubing and container. Although effective for the intended purpose, such rigid-tube catheters have several drawbacks. Normally, the urethra is a closed canal, opening only during the passage of urine, or semen in the male. The mechanism provides a barrier against the introduction of infection for outside the body into the urinary tract. The rigid-tube catheter continuously defeats this mechanism, thus increasing the incidence of infection. With normal body motion, the rigid tube also moves, chafing the urethral epithelium while also transmitting bacteria up into the bladder by a pumping/sliding action. Patient discomfort results, especially when there is a prolonged presence of the catheter.

The present invention is primarily directed to alleviation of the problems of infection and discomfort occasioned by the use of rigid-tube urinary catheters.

SUMMARY OF THE INVENTION

In accordance with one aspect of the invention, there is provided a catheter that permits the continuous collection of urine without the necessity of continually distending the urethra. This is accomplished through the use of a tube having three distinct segments; two relatively short semi-rigid segments separated and joined together by a collapsible intermediate segment. The walls of the rigid tube segments are sufficiently rigid to position, i.e., fix, the ends of the catheter and to defeat the valve-like closing mechanism of the urinary sphincter muscle at the distal end of the catheter and to defeat the normal closing mechanism of the urethral exit at the proximal end of the catheter. When inserted, the collapsible tube extends substantially the entire length of the urethra from a position adjacent the neck of the bladder, and spaced proximally therefrom, to a position spaced inward from the urethral exit. This intermediate section is readily collapsed by the normal urethral closing mechanism. Upon the flow of urine, however, the collapsible tubing is readily distended to the extent necessary to allow the urine to pass. Several important benefits result from the use of the collapsible tubing. First, the collapsible tube tracks the normal response of the urethra to a flow of urine and, thus, avoids the problem of bacterial transmission heretofore encountered in the use of conventional catheters having continuously open channels.

Secondly, and more importantly, the collapsible segment provides no longitudinal rigidity so that body movements and other forces that normally occur on the exterior portion of the catheter cannot be transmitted along the entire length of the catheter. As a consequence, the internal portions of the catheter do not move in response to these forces and thus, do not chafe the patient, nor transmit bacteria via the longitudinal pumping effect occasioned by use of catheters having rigid-walling tubing. In addition, since these use-related external forces cannot dislodge the rigid bladder tube segment of the catheter that holds open the sphincter at the entrance into the bladder, it is not necessary to use complicated, potentially damaging retainers to hold the catheter in place. Instead, and in accordance with an additional aspect of the invention, a simple positioning device, which conforms to the shape of the urinary sphincter, is used in lieu of a retainer to properly position the distal end of the catheter.

Because of the flexibility of the collapsible segment of the catheter, it is necessary to use a special introducer to position the catheter in the bladder. In preferred form, the introducer is a semi-rigid plastic sound, or probe, which is contained, for insertion, within the interior drainage canal of the catheter. After the catheter is in position within the bladder, the sound is removed.

In accordance with additional aspects of the invention, antibacterial seals may be provided on either or both of the rigid segments of the catheter to prevent bacteria from entering around the catheter and to prevent the flow of urine around the catheter. For enhanced bacterial safeguarding, these seals also may be impregnated with bactericides.

According to yet another aspect of the invention, provision is made for an external seal about a portion of the catheter exiting the body. In a preferred form, the external seal forms a pocket having an access port through which bactericidal gels may be introduced as an additional safeguard.

According to still a further aspect of the invention, the relatively short, rigid exit tube is used in conjunction with the external seal to provide an incontinence catheter. This arrangement has several advantages over conventional incontinence catheters of the type in which urine is collected in a condom and then transferred to a collecting bag via rigid tubing. In these known catheters, the tubing often rotates, twisting the condom, and cutting off or restricting the drainage channel. In addition, the urine collected in the condom undesirably remains in contact with the skin and the external urethral orifice. In contrast, the use of the inventive arrangement maintains urine separation from the external seal by collecting the urine from within the urethra and avoids the problem of kinking through the use of the semi-rigid exit tube.

BRIEF DESCRIPTION OF THE DRAWINGS

The invention can best be understood by the following portion of the specification taken in conjunction with the accompanying drawings in which:

FIG. 2 is a perspective view of the distal portion of the catheter showing, in partial section, the retaining head in its radially enlarged position and showing the urethal tube broken and in the collapsed condition;

FIG. 3 is a perspective view similar to FIG. 2 but showing the retaining head radially reduced by the introducer for insertion or retraction;

FIG. 4 is a front sectional view taken along line 4—4 of FIG. 3 showing the collapsible segment in both a collapsed and a partially distended position;

FIG. 10 is a side elevational view, in partial section and with parts broken, showing the catheter of FIG. 8;

FIG. 11 is a side elevation view similar to FIG. 9, but showing the retainer in its expanded condition.

DETAILED DESCRIPTION OF THE PREFERRED EMBODIMENTS

Figure 1:
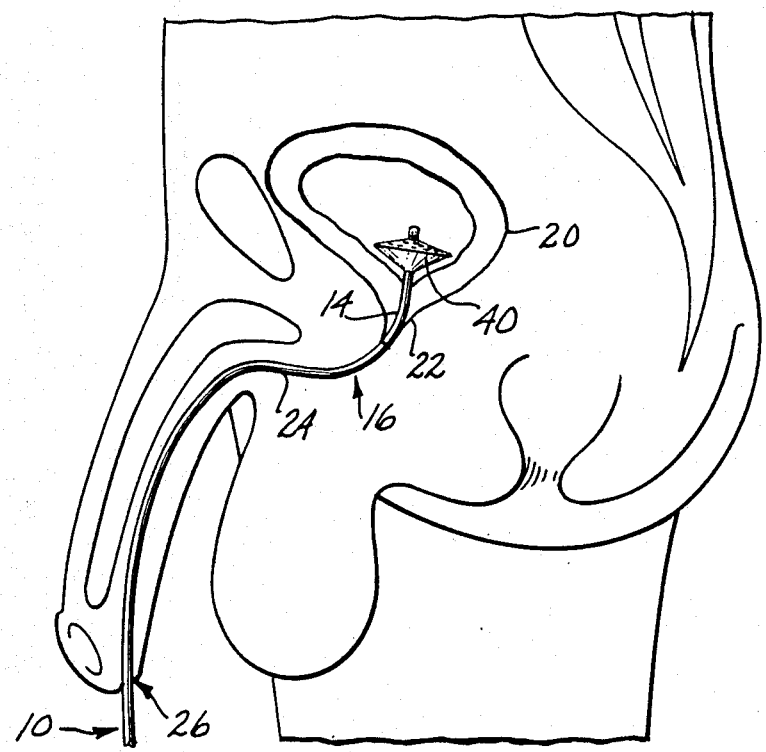
FIG. 1 diagrammatically illustrates a catheter positioned through the urethra and into the bladder.

Referring to FIG. 1, a male version of the catheter 10 of the present invention is shown secured in place within a bladder 20 by a retaining head 40. Urine is drained through an internal channel in the drainage tube portion of the catheter, which extends from retaining head 40 through the bladder neck 22 and outward of the body through the urethra 24 and urethral exit 26.

As shown in FIG. 1, but illustrated in greater detail in FIGS. 2 and 3, two distinct tubular segments constitute the portion of the catheter drainage tube extending from the bladder to the urethral exit 26. A flexible, but axially rigid bladder tube 14 is connected at its distal end to the retaining head 40 and extends from the bladder proximally through the bladder neck 22. The rigidity of bladder tube 14 defeats the valving mechanism of the sphincter, which normally closes the urethra in the area of the bladder neck 22.

A collapsible urethral tube 16 is connected at its distal end to the proximal end of the bladder tube 14. When the catheter is properly inserted, the terminus of the collapsible urethral tube, i.e., its juncture with the bladder tube, is positioned at the beginning of the urethra in the area proximally adjacent the bladder neck. Thus, except for the relatively short bladder-tube retaining head segment, the catheter is predominantly nonrigid throughout its length within the body.

Both the bladder tube 14 and the urethral tube 16 have hollow interiors, or bores, 15 (FIG. 2) and 17 (FIG. 3), respectively, which are interconnected to form an open-ended drainage channel through their combined lengths. In preferred form, the radial dimensions of the bladder tube and urethral tube, as well as the radial dimension of their respective bores, substantially correspond, so that the tubular section of the catheter is substantially uniformly dimensioned both externally and internally. As will be discussed more fully hereinafter, this preferred configuration aids the insertion of the catheter and helps achieve and intended purpose of providing comfort to the patient.

In FIGS. 2 and 3, the scale relative to FIG. 1 has been enlarged and the urethral tube broken near its connection with the bladder tube for purposes of illustration. As shown, the collapsible urethral tube 16 is a relatively thin-walled structure containing a plurality of longitudinal fibers 18 (see also FIG. 4). According to a preferred construction, the urethral tube 16 has flexible walls made of a pliant material, with high tensile strength fibers embedded in the walls and oriented axially about the longitudinal axis of the tube. Preferably, the fibers extend substantially the length of the urethral tube.

As a result of this construction, the urethral tube has significant longitudinal tensile strength and is resistant to outward distension beyond its normal radial dimensions. Importantly, however, the tube is readily collapsed to the position shown in FIGS. 2 and 4 by radially compressive forces. When operatively positioned, the tube 16 is, thus, collapsed by the normal closing mechanism of the urethra, thus closing the bore 17. Upon a flow of urine through the normally distended bladder tube 14, the collapsed urethral tube naturally distends to permit passage of the urine to a suitable conventional sterile collection system, not shown. Since the urethral tube distends only during the passage of urine and only to the extent necessary to allow such passage, the present catheter avoids the problems associated with continuous distension of the urethra occasioned by the use heretofore of rigid-wall catheter tubes. Specifically, the collapse of the urethral tube closes the avenue of bacterial transmission into the body and permits the urethral wall to relax rather than be abnormally and continuously distended. This reduces the incidence of bacterial infection and, as well, diminishes the likelihood of damage to the urethral wall.

The construction of the urethral tube also provides more comfort to the patient. Unlike the known rigid-tube catheters that move within the urethra in response to patient movements, the present urethral tube provides no longitudinal rigidity, i.e., it is not resistant to compression. Thus, forces on the catheter tubing external to the body are not transmitted as damaging or irritating forces on the urethral wall. Avoided, as well, is the characteristic sliding motion of rigid-tube catheters that can transmit bacteria along the urethra. It is to be noted that, while the present urethral tube is not longitudinally rigid, the longitudinal tensile strength imparted by the fibers assures that the internal rigid part of the catheter (the bladder tube) cannot become accidentally disconnected (and thereby permit the entire catheter to be withdrawn simply by tension).

Because of the collapsing and compressing characteristics of the urethral tube, it is necessary to use a removable rigidifying introducer 30 for insertion of the catheter. This introducer 30 is configured to slide easily within the interior of the catheter and may be constructed of any suitable material that is sufficiently rigid to maintain its shape but flexible enough to follow the contours necessary for insertion. A plastic sound is an example of a suitable introducer. As shown in FIG. 3, the introducer 30 also serves to flatten the retaining head 40 for insertion or retraction of the catheter, as will be explained hereinafter.

The urethral tube 16 and longitudinal fibers 18 may be constructed of any suitable materials that exhibit the characteristics described above. For example, this tube may be constructed of an elastomeric or polymeric material (such as one containing organosilicon polymers) with embedded nylon thread. The specific dimensions of the tubing and thread, as well as the number of threads, will be dictated by the particular materials chosen. As long as the desired characteristics are achieved for the urethral tube, it is not essential that the fibers be arranged only longitudinally. It is important, however, that the urethral tube be constructed to exhibit a significant amount of tensile strength in order to withstand the stress exerted on the tube during insertion or withdrawal of the catheter. All such configurations that provide a collapsible tube that is also resistant to longitudinal tensile stress are within the purview of this invention and the appended claims.

As an optional feature, electronic body function sensors and their associated electrical interconnections may be incorporated into the structure of the urethral tube 16 for monitoring purposes. For example, temperature transducers embedded among the longitudinal fibers 18 may be interconnected with external equipment to record or indicate temperature.

The bladder tube 14 may be constructed of any suitable material, such as plastic, which will be sufficiently rigid to effect distension of the bladder opening, yet be sufficiently flexible to facilitate insertion.

To avoid the problems associated with the present balloon retaining devices, it is preferred to use a more passive means for retaining the catheter. In the preferred form, the retaining head, or retainer 40, has opposed, disk-shaped flaps 42 and 43 constructed of a resilient material that are normally retracted, or folded, in the retention mode shown in FIGS. 1 and 2. In this position, the radial dimension of retainer 40 is greater than the radial dimension of bladder tube 14. When so deployed, the proximal surfaces of flap 42 collapse against the interior walls of the bladder to retain the catheter. For draining urine, the distal faces of the flap 43 and the projecting nose 44 have openings 46 communicating with an internal chamber 48 of the retainer. The chamber 48, in turn, has connection with the drainage channel formed by the interconnected bores 15 and 17 in the bladder tube and the urethral tube, respectively.

To insert or withdraw the catheter, the introducer 30 is passed through the drainage channel and into contact with the interior surface of the projecting nose 44. When the introducer is forced distally, the flaps 42 and 43 of the retainer are flattened, thus reducing the radial dimension of the retainer 40. In FIG. 3, the flaps are shown partially flattened. For insertion or withdrawal, it is preferred that the flaps be further flattened so that the radial dimension of the retainer is about the same as the radial dimension of the bladder tube 14. Since the retainer 40 is constructed of a resilient material, when the introducer is withdrawn, the flaps return to the enlarged radial position shown in FIG. 2.

For enhanced protection against bacterial invasion, the catheter may include one or more optional internal seals. Preferably, these seals take the form of sealing rings 50 that encircle the bladder tube 14 distally of its connection with the retainer 40 as shown in FIGS. 2 and 3. Although a plurality of sealing rings is illustrated, it will be appreciated that only one seal could be employed. In addition to providing a barrier to bacteria, sealing rings 50 also help to stabilize the more rigid bladder tube portion of the catheter. For added effectiveness, the seals may optionally be coated or impregnated with a bactericide. Sealing rings constructed of a pervious material, such as plastic foam, are particularly useful for this purpose.

Figure 5:
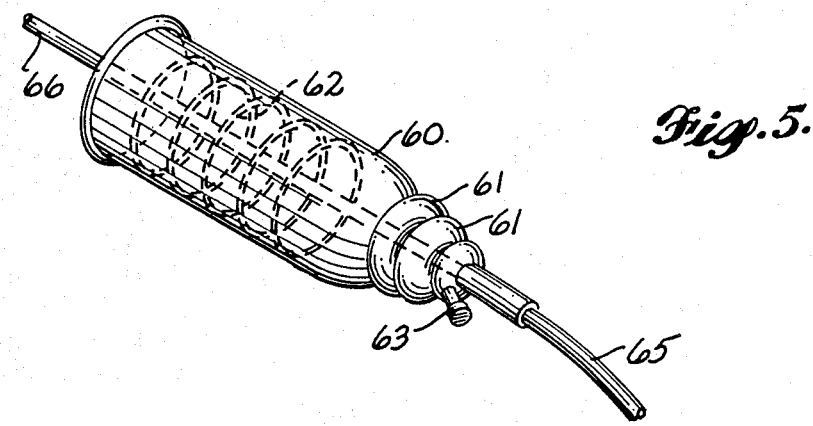
FIG. 5 is a perspective view of a male external seal for the catheter exit site.
Figure 6:
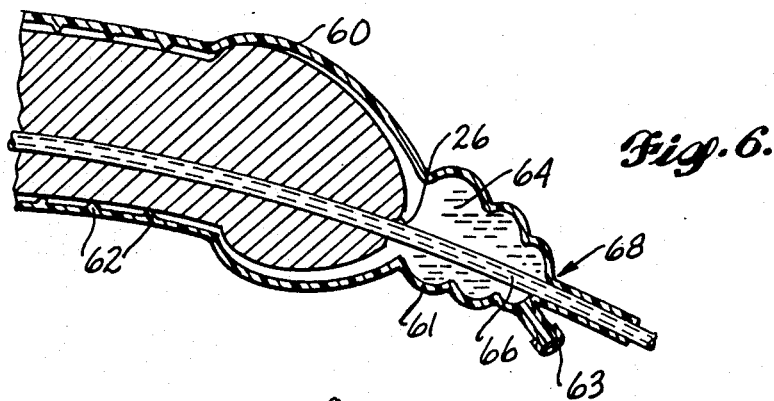
FIG. 6 is a diagrammatic illustration, in side elevational cross section, of the external seal of FIG. 4.

According to yet another aspect of the invention, an external seal is provided for the exit site of the catheter as it leaves the body. These seals have the twofold purpose of minimizing the entry of bacteria into the urethra and minimizing transmission of motion and tension on the external portion of the catheter to the portion of the catheter within the body. In general, these seals are constructed of a pliant material that will fit snugly to the skin surrounding the exit site of the catheter. As well, the seals are configured to confirm to the anatomy of the exit site for a male or female patient. Referring initially to the male version illustrated in FIGS. 5 and 6, the external seal 60 has corrugations or ridges 62 (FIG. 6) at its points of contact with the body skin in order to enhance an airtight adhesion. Proximally outward from the urethral exit 26, the seal forms an internal pocket 64 that completely surrounds the portion of the catheter tube 66 as it leaves the body. Although in FIG. 6 tube 66 is shown to be a continuous tube, which, for example, could be the continuation of the collapsible urethral tube 16, it is to be understood that there could be an interconnection of the urethral tube 16 with the tubing 65 leading into the collection system (as illustrated in FIG. 5). Optionally, the junction of the interconnection also could be contained within the internal pocket 64. At its proximal end 68, the external seal 60 has a fluid-tight connection with the catheter tube 66. Extending distally from this connection, is a concertina configuration of accordian pleats, or folds, 61. The conjunction with the fluid-tight pocket 64, the accordian folds 61 function to dampen external forces applied to the catheter tube 66. For example, tension on the catheter will extend the accordian folds, creating a fluid force within the pocket 64, which will draw the external seal inwardly at its points of contact with the skin, for example, adjacent the sealing ridges 62. This effect increases the adhesion between the seal and skin, thus minimizing bacterial entry into the pocket. As well, the arrangement effects the transmission of tension on the catheter tube to the surface of the patient's body.

As an additional safeguard, bactericidal gels may be contained with the pocket 64. Such gels will prevent bacterial entry to the urethral exit 26, provide abrasion-avoiding lubrication between the seal and the skin, and enhance the establishment of a fluid-tight seal between the seal and skin. Optionally, the seal 60 may include an injection port 63 for the sterile introduction or replenishment of sealing gel within the pocket 64. Provision of the injection port prolongs the effectiveness of the external seal without risk of contamination.

Figure 7:
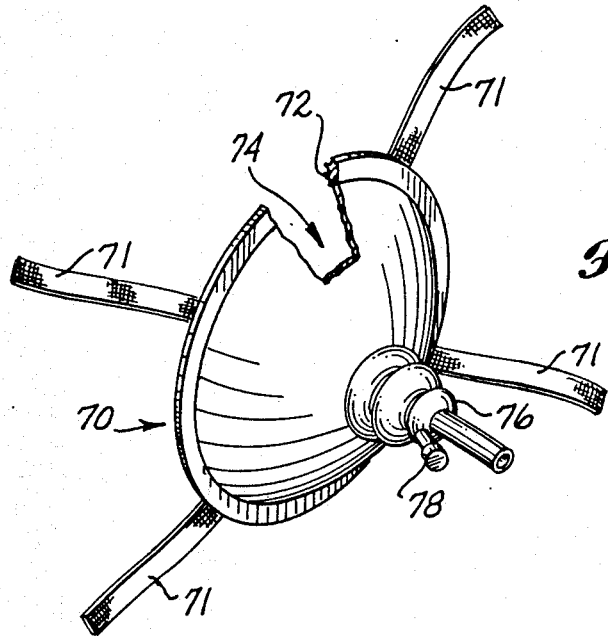
FIG. 7 is a diagrammatic perspective view of a female external seal for the catheter exit site.

The female version of an external seal 70 illustrated in FIG. 7 functions in a similar fashion to the male version just described, differing only in its configuration to conform to the female rather than the male external anatomy adjacent the urethral exit. In this regard, sealing ridges 72 functionally correspond to the ridges 62 in the male version to enhance a fluid-tight seal between the seal 70 and the skin. Identical functional correspondence is likewise found between bactericidal gel pocket 74 and pocket 64, accordian pleats 76, and pleats 61, and between injection port 78 and injection port 63. In contrast to the male embodiment of the external seal, the female version of the seal includes adhesive retaining straps 71 to assist in holding the device to the patient's body.

As noted above, an important aspect of the invention is to eliminate the problem of urethral chafing by preventing external forces acting on portions of the catheter outside of the body from being transmitted to the portions of the catheter that are positioned within the body. In the embodiments described above, this is principally accomplished through the use of a catheter having a rigid tubular portion for holding open the entrance of the bladder and a collapsible tubular portion that has no longitudinal rigidity and, thus, is incapable of transmitting external forces to the bladder tube.

Figure 8:
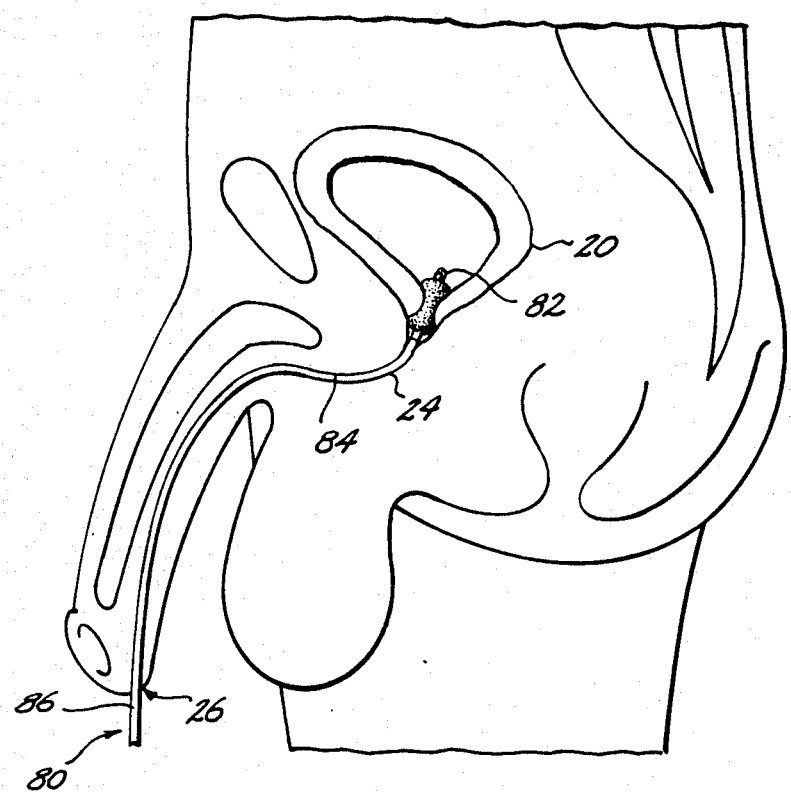
FIG. 8 diagrammatically illustrates a modified form of a catheter according to the invention positioned through the urethra and into the bladder.

FIGS. 8 through 12 illustrate a modified form of catheter according to the invention that also avoids the transmission of forces along the entire length of the catheter. As shown in FIG. 8 and illustrated in greater detail in FIG. 10, the catheter 80 has three distinct segments; a semi-rigid bladder tube 82 at the distal end of the catheter, an intermediate, collapsible urethral tube 84, and a semi-rigid exit tube 86 at the proximal end of the catheter. The bladder tube 82 is of similar construction to the bladder tube 14 discussed above, being flexible, but axially rigid to defeat the valving mechanism of the urinary sphincter. As shown best in FIGS. 10 and 11, the distal end of the bladder tube has openings 88 that communicate with an internal bore 90 that passes through the length of the tube.

The tubing that passes through the urethra is also essentially unchanged from the embodiment discussed above, except that the segment that passes through the external urethral orifice is noncollapsible. Also unchanged in this embodiment are the external seals 60 and 70. The rigidity of the segment at the external orifice, however, permits external connections to drainage tubes to be made, prevents torsion and kinking of the urethral tube as it exits the urethra, and permits additional sealing rings or cushions to occupy the space between the catheter and the urethra adjacent the external exit of the urethra. This further enhances the bacterial seal at the external exit site previously described.

The collapsible urethral tube 84 has an internal bore 85 that is connected with the bore 90 of the bladder tube and is of the same construction as the collapsible urethral tube 16 of the FIG. 1 embodiment. Thus, although not shown in FIGS. 10 through 12, the urethral tube preferably includes a plurality of fibers that inpart tensile strength so that the tube will not break under the stresses exerted thereon during insertion or withdrawal of the catheter. As will be discussed in greater detail hereinafter, the exit tube 86 is also rigid and, thus, functions to fix the proximal end of the catheter. Since the bladder tube 82 fixes the opposite, i.e., distal, end of the catheter it is desirable to arrange the fibers in the urethral tube so that this tube has a measure of longitudinal elasticity in order to adjust to, or accommodate, variations in the length of the urethra that occur as the penis changes length. One way of achieving this is to arrange the fibers in a gently curving spiral so that the urethral tube may be stretched longitudinally a predetermined distance until the fibers are straightened. After reaching this extension threshold, then the tube resists further longitudinal extension and thus, can be easily withdrawn.

The exit tube 82 is constructed similarly to the bladder tube, being somewhat flexible for insertion purposes yet having axially rigid walls that hold open the urethral exit. This tube includes an interior bore 87 that is interconnected with the bores 90 and 85 of the bladder tube and urethral tube, respectively, to form a continuous open-ended drainage channel. It will readily be understood that the flexible urethral tube necessitates the use of an introducer, such as introducer 30, for inserting the catheter. As a consequence, it is preferred that the radial dimensions of the internal bores of each of the three tubes substantially correspond.

The lengths of the bladder tube 82 and the exit tube 86 are selected to be as short as is possible without losing their effectiveness so that the collapsible urethral tube 84 constitutes the significant portion of the catheter within the urethra. When the catheter is properly inserted, the bladder tube 82 extends from the bladder proximally through the bladder neck to a position that is adjacent the bladder neck and spaced proximally therefrom. In this position, the bladder tube forces open the sphincter 92 (see FIG. 11). At the other end of the catheter, the exit tube 86 is connected at its distal end to the proximal end of the urethral tube 84 at a position spaced inward from the urethral exit 26. The position of this junction between the urethral tube and the exit tube is selected so that the exit tube forms its intended function of positioning, i.e., fixing, the proximal end of the catheter such that the catheter cannot be accidentally withdrawn by bodily movement or by extension or retraction of the penis.

In conventional catheter, it is necessary to include retaining devices such as an inflatable balloon to maintain the catheter in position and prevent its accidental withdrawal. An important advantage of the catheter 80 is that the two rigid segments are separated by a limp, flexible intermediate tube. As a consequence, the bladder tube 82 is not disturbed by the pushing, pulling, and rotational forces that act upon the exit tube (other than those applied specifically for insertion or withdrawal). As noted earlier, this prevents chafing of the urethra. An equally important benefit flowing from the lack of forces on the bladder tube is that it is not necessary to include complicated retaining devices to hold the catheter within the bladder. Rather, it is necessary to utilize only a simple positioning device to set the proper location of the bladder tube so that its distal end and the openings 88 are within the bladder. Referring again to FIGS. 10 and 11, the preferred positioning device is a conformable seal 94 that encircles the outer periphery of the bladder tube 82. The seal is formed of a material that is compressible to a low-profile configuration, as shown in FIG. 10, for insertion and expandable in dumbbell fashion around the sphincter 92 as shown in FIG. 11 to properly position the bladder tube. To hold the seal 94 in its compressed condition, the catheter may include a removable sheath 96. After insertion, the removable sheath 96 is retracted away from the seal, as shown in FIG. 11, so that the seal may naturally expand. The sheath may either by fully retracted the entire length of the catheter or suitably arranged for partial retraction to an extend sufficient to remove it from the seal 44.

Figure 9:
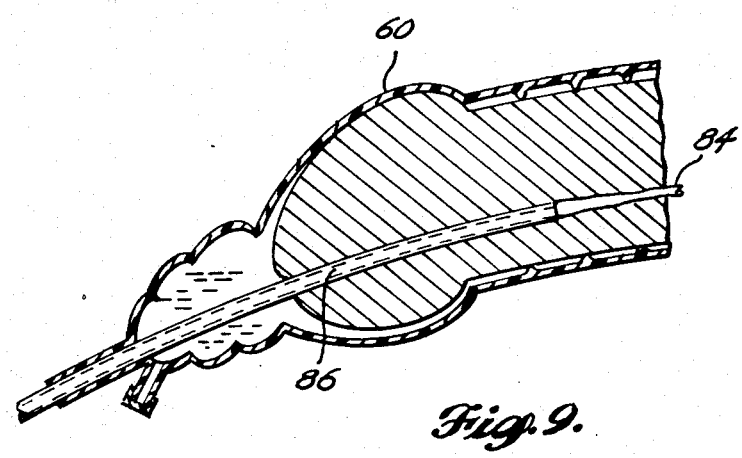
FIG. 9 is diagrammatic illustration, in side elevational cross section of the external seal of FIG. 4 used with the catheter of FIG. 8.

Referring now to FIG. 9, the modified catheter 80 may also include an external seal for the exit area of the catheter. These seals can be configured identical to the male and female seals 60 and 70, respectively, of FIGS. 6 and 7. These arrangements will be readily understood from FIG. 9, which shows the male version of an external seal 60 used in conjunction with the modified catheter 80.

In order to monitor deep body temperature, the catheter 80 includes, as an optimal feature, a temperature transducer 100 at the distal end of the bladder tube 82. Electrical conductors, not shown, connect the transducer 100 to external monitoring equipment.

Figure 12:
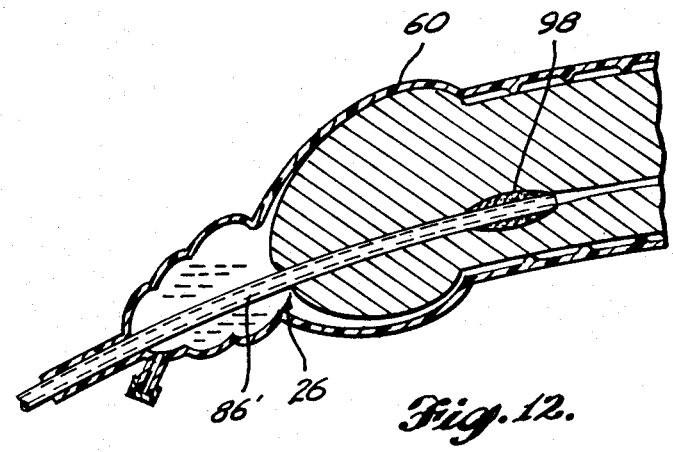
FIG. 12 is a diagrammatic illustration, in side elevational cross section of an incontinence catheter according to the invention.

According to yet another aspect of the invention, the semi-rigid exit tube 86 can be used alone in combination with the external seal 60 or external seal 70 to provide an incontinence catheter. FIG. 12 illustrates the male version of an incontinence catheter having an exit tube 86' and an external seal 60. As indicated by the use of like numerals to identify common structural components, the seal 60 is identical in all respects to the seal 60 of FIG. 6. The exit tube 86' extends into the urethra from outside the body, terminating at a position spaced inward from the urethral exit 26. The length of the exit tube 86' is selected to be sufficient so that the tube is not accidentally withdrawn by motion or tension on the external portion of the catheter.

The purpose of the semi-rigid exit tube 86' within the urethra is identical to its purpose in the previously described catheter 80, namely to provide a sterile passage that is in continuity with the urethra and that can communicate directly with external drainage devices. The rigidity of the tube prevents kinking thereof and provides resistance to a torsion. This torsional resistance prevents the drainage channel from becoming obstructed as a result of the continuous rotation of externally connected device, such as drainage tubes.

Since the urethra naturally distorts with a flow of urine, there may be the likelihood, particularly under the pressure of a forced urination, for the urine to flow around the distal end of the exit tube and into the internal pocket 64. If this occured, then urine would undesirably come into contact with the skin and contaminate any bactericidal gel that may be contained within the pocket 64. To prevent this from occurring, the distal end of the exit tube preferably includes a conformable, peripheral seal 98 that ensures that urine will flow through the exit tube rather than around it. This peripheral seal may be of a type such as the sealing rings 50 that encircle the bladder tube 14 discussed above. Alternatively, and as shown in FIG. 12, the peripheral seal may have a generally tubular shape and be constructed from an expandable material. It will be appreciated that many other forms of seals may be substituted for the peripheral seal 98 and still satisfy the aim of sealing the space between the exit tube and the distensible urethra in order to prevent bacterial entry into the urethra around the catheter and to prevent urine from leaking around the incontinence catheter.

The present invention has been described in relation to its preferred embodiment. One of ordinary skill, after reading the foregoing specification, will be able to effect various changes and substitutions of equivalents without departing from the broad concepts disclosed herein. It is therefore intended that the protection afforded by Letters Patent granted hereon be limited only by the definition contained in the appended claims and equivalents thereof.

The embodiments of the invention in which an exclusive property or privilege is claimed are defined as follows:

1. A urinary catheter comprising:
   a noncollapsible exit tube, said exit tube having an internal bore and being of sufficient length to extend through a portion of the urethra and out of the body from a position spaced inward from the urethral exit;
   a noncollapsible bladder tube, said bladder tube having an interior bore and being of sufficient length to extend into the bladder from the area adjacent the bladder neck;
   a urethral tube having an interior bore, said urethral tube being connected at its proximal end to the distal end of said exit tube and connected at its distal end to the proximal end of said bladder tube, said tube being constructed of a pliant material and having fibers therein, said tube being normally collapsed within the urethra but radially distended by a flow of urine through the bore, said interior bore being closed when said tube is collapsed and open when said tube is radially distended, the interior bore of said urethral tube being cooperatively connected with the interior bores of said exit tube and said bladder tube to form a drainage channel; and
   an external seal disposed in sealing engagement about a portion of the periphery of said exit tube outside of the body and in conforming, sealed engagement with the exterior anatomy, said seal forming a pocket about the exterior anatomy when said catheter is positioned in place, said seal including accordian folds disposed between the respective points of engagement of said seal with said exit tube and said anatomy, said folds being extensible and distensible in response to movement of said exit tube, said seal including an injection port providing fluid access to said pocket.

2. A urinary catheter comprising:
   a noncollapsible tube, said tube having an interior bore and being of sufficient length to extend through a portion of the urethra and out of the body from a position spaced distally inward from the urethral exit;
   an internal seal disposed about a portion of the periphery of said tube so as to be positioned distally inward from the urethral exit when said catheter is positioned in place; and
   an external seal disposed in sealing engagement about a portion of the periphery of said tube outside of the body and in conforming, sealed engagement with the exterior anatomy, said seal forming a pocket about the exterior anatomy when said catheter is positioned in place, said external seal including accordion folds disposed between the respective points of engagement of said seal with said tube and said anatomy, said folds being extensible and distensible in response to movement of said tube, said external seal having an injection port providing fluid access to said pocket.

* * * * *

UNITED STATES PATENT AND TRADEMARK OFFICE
CERTIFICATE OF CORRECTION

PATENT NO.   :   4,710,169

DATED        :   December 1, 1987

INVENTOR(S)  :   T. Graham Christopher

It is certified that error appears in the above-identified patent and that said Letters Patent is hereby corrected as shown below:

```
Column 1, line 17, "in" should be --In--
Column 1, line 18, "or" should be --of--
Column 1, line 27, "thickwalled" should be --thick-walled--
Column 6, line 20, "confirm" should be --conform--
Column 6, line 40, "The" should be --In--
Column 6, line 53, "with" should be --within--
Column 7, line 53, "inpart" should be --impart--
Column 8, line 34, "catheter" should be --catheters--
Column 8, line 64, "extend" should be --extent--
Column 9, line 34, "device" should be --devices--
```

Signed and Sealed this

Twenty-seventh Day of September, 1988

*Attest:*

DONALD J. QUIGG

*Attesting Officer*        Commissioner of Patents and Trademarks